(12) United States Patent
Harbers

(10) Patent No.: US 9,285,311 B2
(45) Date of Patent: Mar. 15, 2016

(54) SYSTEM FOR PERFORMING SCATTERING AND ABSORBANCE ASSAYS

(75) Inventor: Rik Harbers, Zurich (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 867 days.

(21) Appl. No.: 13/274,678

(22) Filed: Oct. 17, 2011

(65) Prior Publication Data
US 2012/0120388 A1 May 17, 2012

(30) Foreign Application Priority Data

Oct. 29, 2010 (EP) .................................... 10189450

(51) Int. Cl.
*G01N 21/00* (2006.01)
*G01N 15/02* (2006.01)
*G02F 1/01* (2006.01)
(Continued)

(52) U.S. Cl.
CPC ................ *G01N 21/51* (2013.01); *G01N 21/59* (2013.01)

(58) Field of Classification Search
CPC ................ G01N 21/47; G01N 21/49; G01N 2021/4804; G01N 21/59; G01N 2021/5969; G01N 2015/0092; G01N 2021/4704; G01N 2021/4742; G01N 2021/1782; G01N 2021/4707; G01N 21/51; G01N 21/253; G01N 21/6452; G01N 21/6445; G01J 3/42; Y10S 436/805; Y10S 435/808
USPC .................... 356/73, 336, 338; 250/573, 225; 385/12; 422/73, 82.05, 82.09; 436/523, 436/533, 534, 805
See application file for complete search history.

(56) References Cited

U.S. PATENT DOCUMENTS 5,286,452 A * 2/1994 Hansen ........................... 422/73
5,762,878 A * 6/1998 Clark et al. .................... 422/549
(Continued)

FOREIGN PATENT DOCUMENTS

JP 60-159635 A 8/1985
JP 10-227738 A 8/1998
(Continued)

OTHER PUBLICATIONS

Kim, Yoen Jee et al., "Data preprocessing and partial least squares regression analysis for reagentless determination of hemoglobin concentrations using conventional and total transmission spectroscopy," Journal of Biomedical Optics, 2001, pp. 177-182, vol. 6, No. 2.

*Primary Examiner* — Tarifur Chowdhury
*Assistant Examiner* — Sunghee Y Gray
(74) *Attorney, Agent, or Firm* — Roche Diagnostics Operations, Inc.

(57) ABSTRACT

An optical system for performing scattering and absorbance assays in clinical diagnostics comprises a light source for emitting collimated light parallel to an optical axis in an optical path, a sample holding unit comprising at least one sample holding position located in the optical path and an optical detector for measuring light transmitted through a sample located in a sample holding position. The optical system further comprises an adjustable light angle selector adjusted to prevent light transmitted through the sample and diverging from the optical axis with an angle greater than a certain value from reaching the detector when a scattering assay is performed, and wherein the light angle selector is adjusted to allow light transmitted through the sample and diverging from the optical axis with an angle smaller than a certain value to reach the detector when an absorbance assay is performed.

8 Claims, 5 Drawing Sheets

(51) Int. Cl.
  *G02B 6/00* (2006.01)
  *G01N 33/543* (2006.01)
  *G01N 33/546* (2006.01)
  *G01N 33/53* (2006.01)
  *G01N 21/51* (2006.01)
  *G01N 21/59* (2006.01)

(56) References Cited

U.S. PATENT DOCUMENTS

| | | |
|---|---|---|
| 5,898,487 A | 4/1999 | Hage |
| 6,791,676 B1 | 9/2004 | Meller |
| 6,982,431 B2 * | 1/2006 | Modlin et al. ............... 250/573 |
| 7,830,518 B2 | 11/2010 | Kanayama |
| 8,908,175 B1 * | 12/2014 | Kandel et al. ............... 356/323 |
| 2004/0195511 A1 * | 10/2004 | Elmore et al. ........... 250/339.02 |
| 2007/0201788 A1 * | 8/2007 | Liu et al. ......................... 385/12 |
| 2007/0222984 A1 | 9/2007 | Palumbo |
| 2009/0185163 A1 * | 7/2009 | Shimazu et al. ............... 356/51 |
| 2010/0020308 A1 | 1/2010 | Wells et al. |

FOREIGN PATENT DOCUMENTS

| | | |
|---|---|---|
| JP | 2002-48714 A | 2/2002 |
| WO | 2009014866 A1 | 1/2009 |

* cited by examiner

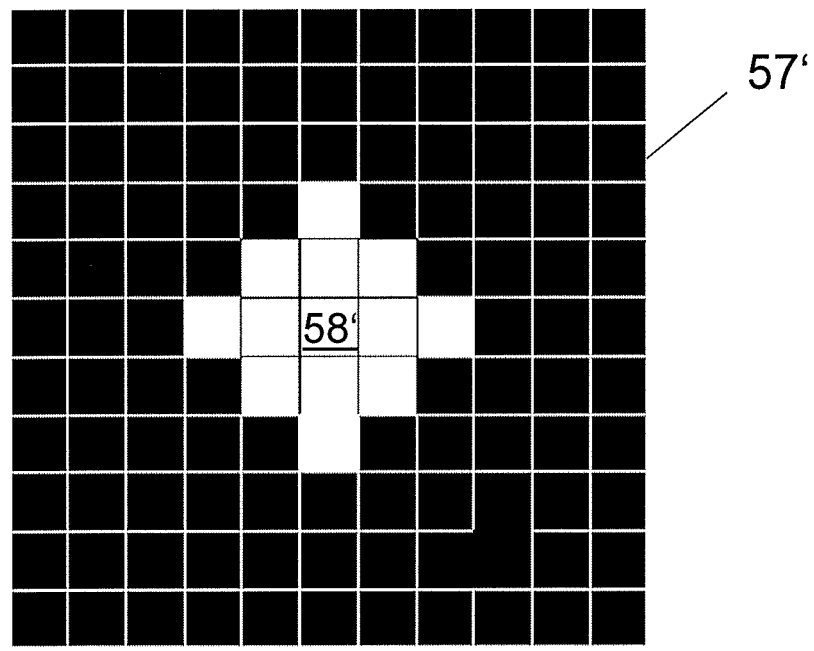
FIG. 6a
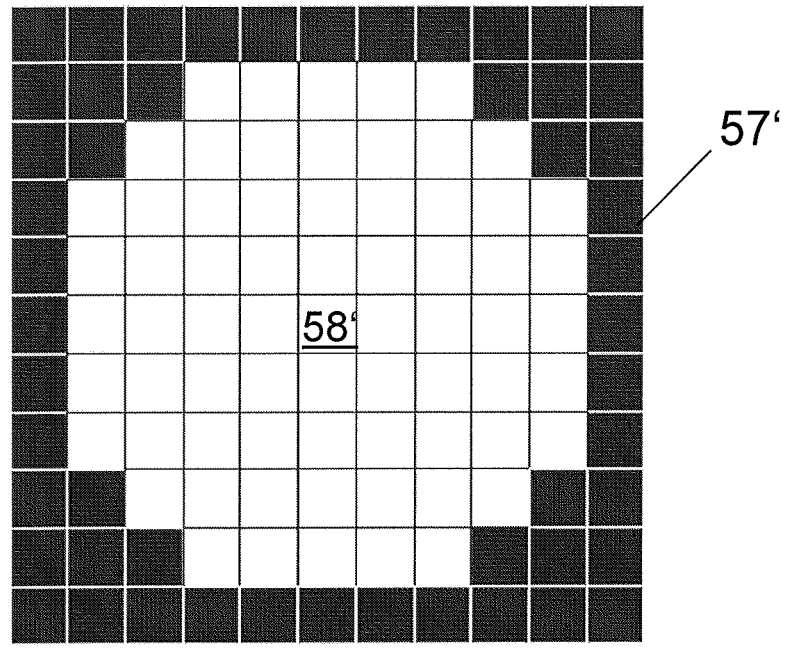
FIG. 6b
FIG. 6

SYSTEM FOR PERFORMING SCATTERING AND ABSORBANCE ASSAYS

FIELD OF THE INVENTION

The present invention is in the field of optical systems and methods for performing scattering and absorbance assays in clinical diagnostics, wherein scattering substances may interfere with absorbance assays.

BACKGROUND OF THE INVENTION

Several instruments used in the analysis of samples, such as biological samples, comprise a light source to illuminate the sample and an optical detector to perform a photometric measurement. In clinical chemistry and some immunochemistry assays, for example, the optical transmission of a liquid sample is measured through a cuvette. The results are used to generate extinction data, which is the ratio between light intensity input and light intensity after transmitting the sample. Optical extinction can be caused either by absorbance or by scattering of the light by the sample. In the case of absorbance, extinction is caused by the selective absorbance of light by a particular substance typically at selected wavelengths. In the case of scattering, extinction is caused by the light being deviated in all directions by particles or drops in the carrier liquid. Scattering is typically independent from the wavelength. Particularly, scattering can be used to measure the concentration of macromolecules or particles in solution. Given a fixed total concentration of one or more species, scattering signal is a direct measure of the weight-averaged molar mass of the solution, which will vary as complexes form or dissociate. Therefore, reagents which form complexes with analytes present in a sample, such as latex beads whose surface has been derivitized with analyte binding groups, are typically used in this type of assays, also called turbidimetric assays.

In this way, the presence and/or concentration of analytes in a sample, which may be indicative of a clinical diagnostic condition, can be determined by measuring response signals.

Both forms of extinction measurements, absorbance and scattering, suffer from possible interferences, i.e., undesired substances in the sample, which may lead to deviations or errors in the measurement.

In scattering assays, extinction is due to scattering caused by a substance of interest in the sample or like in turbidimetric assays by reaction processes between the substance of interest and one or more reagents. The measurement however may be erroneous in the case of, for example, lipemic samples. Lipids suspended in samples are known to also cause scattering and, thus, to interfere with the measurement of the substance of interest.

Another type of interference in scattering assays is an absorbing substance that interferes with measurement of scattering. However as scattering can be observed at any wavelength and the absorbing interference is usually confined to a specific wavelength range, it is usually possible to circumvent the interference by a suitable choice of measurement wavelengths.

An interference in absorbance assays is due to scattering caused by undesired substances such as lipids in lipemic samples, which disturbs the absorbance measurement.

Since a scattering interference is present at all wavelengths, sensitivity to scattering automatically causes disturbance of absorbance assays.

SUMMARY OF THE INVENTION

It is against the above background that the present invention provides certain unobvious advantages and advancements over the prior art. In particular, the inventor has recognized a need for improvements in systems and methods for performing scattering and absorbance assays.

Although the present invention is not limited to specific advantages or functionality, it is noted that the present invention provides an optical system, which is optimized for both scattering and absorbance assays. This is achieved by means of a light angle selector in the optical system, which is adjusted to let a small divergence of a collimated light to be detected when a scattering assay is performed, and is adjusted to allow stronger diverging light to reach the detector when an absorbance assay is performed.

In accordance with embodiments of the present invention, sensitivity to scattering can be maintained when a scattering assay is being performed while sensitivity to scattering can be removed or diminished when an absorbance assay is being performed, thus resulting in lesser sensitivity to scattering interferences. In other words the influence of scattering interferences on absorbance assays can be reduced without impairing sensitivity in scattering assays.

Since the present invention allows the use of the same optical system and/or the same instrument for both scattering and absorbance assays, cost savings, space savings and reduction of complexity may also be achieved.

In accordance with one embodiment, an optical system for performing scattering and absorbance assays in clinical diagnostics is provided, the optical system comprising: a light source for emitting collimated light parallel to an optical axis in an optical path, a sample holding unit comprising at least one sample holding position, an optical detector for measuring light transmitted through a sample being located in the optical path in the sample holding position, and an adjustable light angle selector. The adjustable light angle selector comprises at least one of the following: at least one lens with a focal length (f) and a diaphragm with variable aperture or an LCD with switchable pixels, located at the focal length (f); a group of lenses and a driver for varying the relative distance between lenses as a zoom objective with variable focal length (f); and a driver for varying the relative distance between the sample holding position and the detector along the optical axis. For a scattering assay, the light angle selector is adapted to be adjusted such as to allow only light transmitted through the sample and diverging from the optical axis with an angle ($\alpha$) less than about 5 degrees to reach the detector. For an absorbance assay, the light angle selector is adapted to be adjusted such as to allow light transmitted through the sample and diverging from the optical axis with an angle ($\alpha$) less than about 60 degrees to reach the detector.

In accordance with another embodiment, a method for performing scattering and absorbance assays in clinical diagnostics is provided, the method comprising the steps of: emitting collimated light from a light source parallel to an optical axis in an optical path; measuring light with a detector transmitted through a sample being located in the optical path in a sample holding unit; adjusting a light angle selector such as to allow only light transmitted through the sample and diverging from the optical axis with an angle ($\alpha$) less than about 5 degrees to reach the detector when a scattering assay is being performed; or adjusting said light angle selector such as to allow light transmitted through the sample and diverging from the optical axis with an angle ($\alpha$) less than about 60 degrees to reach the detector when an absorbance assay is being performed.

In accordance with yet another embodiment of the invention, an instrument for performing scattering and absorbance assays in clinical diagnostics is provided, the instrument comprising: an optical system as described herein, a sample holding unit for receiving samples to be assayed, a reagent holding unit for holding reagents to perform the assays, a cuvette feeding unit for feeding optical cuvettes to the sample holding unit, and a liquid processing unit to deliver samples and/or reagents to optical cuvettes.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIGS. 6a and 6b refer schematically to a forth type of adjustable light angle selector according to another embodiment of the present invention.

Figure 1:
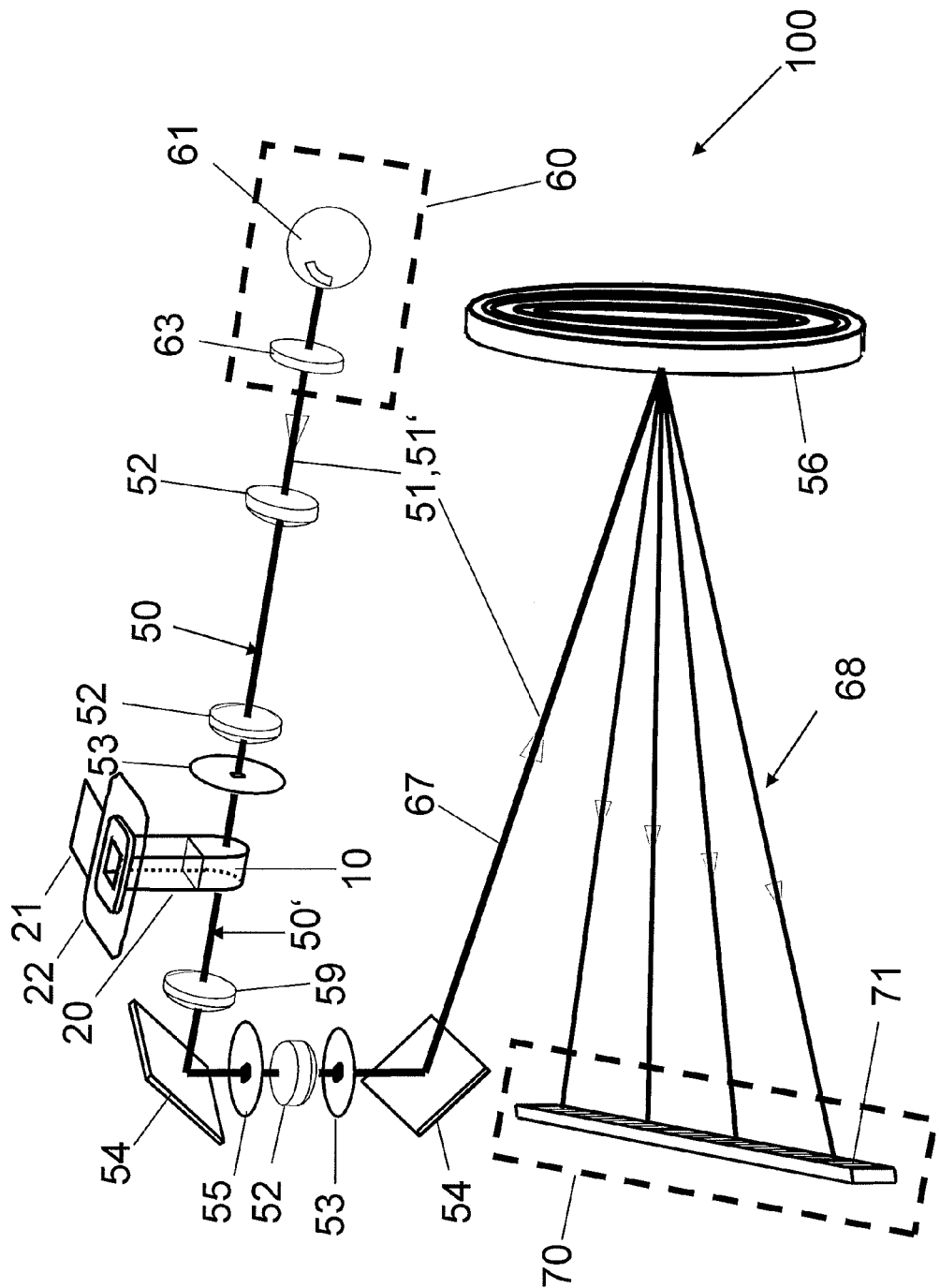
FIG. 1 depicts schematically an optical system according to an embodiment of the present invention for performing scattering and absorbance assays in clinical diagnostics.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DESCRIPTION OF THE INVENTION

The present invention relates to an optical system for performing scattering and absorbance assays in clinical diagnostics. The optical system comprises a light source for emitting collimated light parallel to an optical axis in an optical path, a sample holding unit comprising at least one sample holding position, and an optical detector for measuring light transmitted through a sample being located in the optical path in a sample holding position. The optical system further comprises an adjustable light angle selector comprising at least one of the following:

at least one lens (59) with a focal length (f) and a diaphragm (57) with variable aperture (58) or an LCD (57') with switchable pixels, located at the focal length (f), a group of lenses (80, 81, 82) and a driver for varying the relative distance between lenses as a zoom objective (83) with variable focal length (f), a driver (84) for varying the relative distance between the sample holding position (22) and the detector (70) along the optical axis (51).

For a scattering assay the light angle selector is adapted to be adjusted such as to allow only light transmitted through the sample and diverging from the optical axis with an angle less than about 5 degrees to reach the detector.

For an absorbance assay the light angle selector is adapted to be adjusted such as to allow light transmitted through the sample and diverging from the optical axis with an angle less than about 60 degrees to reach the detector.

According to a typical embodiment, for a scattering assay the light angle selector is adapted to be adjusted such as to allow only light transmitted through the sample and diverging from the optical axis with an angle of about 3 degrees or less to reach the detector.

An optical system, according to the present invention, can be either a separate unit or an integrated component or module within an analytical instrument. Particularly, the optical system makes it possible to guide light in a controlled manner through a sample located in a sample holding unit, and to measure changes in optical transmission, such as absorbance and scattering, for the optical analysis of analytes present in the sample. The optical system unit may however be configured to carry out in addition other spectroscopic measurements. It may also entail temporally static measurements, time resolved measurements, or both.

A sample holding unit is an assembly comprising at least one sample holding position. The sample holding position may be adapted as a vessel, tube or channel to receive directly a sample to be assayed. Alternatively, the sample holding position may be adapted as a receptacle, frame or arm to receive a sample vessel, e.g., an optical cuvette, the sample being located in the cuvette.

The sample holding unit may be embodied as a conveyor, e.g., a linear or rotor-like conveyor, moving in at least one direction or as a robotic arm capable of performing movements along, driven by one or more electrical motors. According to one embodiment, the sample holding unit comprises an array of sample holding positions, the sample holding positions being located in the optical path one at a time according to an established assay sequence. According to another embodiment, the sample holding unit is assembled as a rotor comprising a plurality of sample holding positions to receive a plurality of optical cuvettes and to bring one cuvette at a time in the optical path, i.e., in optical alignment with the other components of the optical system.

The optical system is configured for analyzing, e.g., biological samples. Samples are typically liquid solutions in which one or more analytes of interest can be potentially found, such as, e.g., body fluids like blood, serum, plasma, urine, milk, saliva, cerebrospinal fluid, etc. Samples may be analyzed as such or after being diluted with another solution, or after having been mixed with reagents, e.g., to carry out one or more diagnostic assays like, e.g., clinical chemistry assays and immunoassays. The optical system may advantageously be used in the performance of scattering assays to detect the result of a chemical or biological reaction or to monitor the progress of a chemical or biological reaction, e.g., in a coagulation assay, agglutination assay, or turbidimetric assay. Examples of analytes being determined by scattering assay are D-Dimer and C-reactive protein (CRP), just to cite a few. The optical system may also be configured for use in the performance of absorbance assays for the qualitative and/or quantitative analysis of clinical chemical analytes such as albumin and Glucose, among many other examples of analytes. Thus, depending on the analyte to be determined, the optical system according to embodiments of the present invention may be switched into a scattering assay mode or an absorbance assay mode.

A light source, according to an embodiment of the invention, is a unit within the optical system capable of emitting collimated light in a usable range. The term "usable" refers to a selected wavelength or wavelength range, at which light guided through a sample can be used to measure analyte concentrations present in the sample.

The light source comprises at least one light emitting element. A light emitting element is an electric powered radiation source such as, i.e., an incandescent lamp, an electroluminescent lamp, a gas discharge lamp, a high-intensity discharge lamp, or a laser.

According to one embodiment, the at least one light emitting element is for example a halogen lamp, which like all incandescent light bulbs, produces a continuous broad spectrum of light, from near ultraviolet to far infrared.

According to another embodiment, the at least one light emitting element is a light emitting diode or "LED". LEDs are typically inorganic semiconductor diodes that convert applied electrical energy to light. LEDs may also be Organic Light Emitting Diodes (OLED), that can be polymer-based or small-molecule-based (organic or inorganic), edge emitting diodes (ELED), Thin Film Electroluminescent Devices (TFELD), Quantum dot based inorganic "organic LEDs", and phosphorescent OLEDs (PHOLED).

Collimated light is light whose rays are nearly parallel, and therefore will disperse minimally with distance. Light can be collimated by a number of processes, for instance by means of collimators known in the field of optics, such as collimating lenses and mirrors.

According to certain embodiments, the light source comprises a collimator for collimating emitted light. According to another embodiment, the light emitting element is capable of emitting light, which is already collimated. This is for example the case for some laser sources.

An optical detector according to embodiments of the present invention is a photodetector, which is a device that converts electro-magnetic energy into an electrical signal, including both single element and multi-element or array optical detectors. Thus an optical detector is a device capable of monitoring an optical electro-magnetic signal and providing an electrical output signal or response signal relative to a baseline signal indicative of the presence and/or concentration of an analyte in a sample being located in the optical path. Such devices include, for example, photodiodes, including avalanche photodiodes, phototransistors, photoconductive detectors, linear sensor arrays, CCD detectors, CMOS optical detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrating circuit. Suitable pre-preamplifiers include integrating, transimpedance, and current gain (current mirror) pre-amplifiers. According to one embodiment, the detector is of the CCD or CMOS type. According to another embodiment the detector is of the photodiode or PMT type.

The optical path is an optical construction, which makes it possible to guide light in a controlled manner along an optical axis from the light source through a sample located in the sample holding unit and to an optical detector. The optical axis is an imaginary line, which represents the average path followed by light when travelling from the light source to the detector. The optical path may comprise components such as lenses, mirrors, apertures, filters, a shutter, a heat shield, fiber optics, a light mixing element, a dispersion element, etc. A dispersion element may be a transmission or reflection diffraction grating, and may be a scanning monochromator or a polychromator, which is configured to receive transmitted light and disperse it into multiple spectral components. A dispersion element may be also a refractive element, such as a prism. According to various embodiments of the present invention, the optical system further comprises an adjustable light angle selector. A light angle selector is a device with at least one moving component, which depending on the movement has an effect on the portion of light transmitted through a sample that reaches the detector. In particular, a light angle selector has the function to select light rays emanating from a sample according to their angle of divergence from the optical axis. In order to detect even small divergences from the optical axis due to scattering of substances in the sample and not to the direction of the incoming light, the sample is illuminated with collimated light parallel to the optical axis. In absence of scattering substances in the sample the collimated light rays will remain parallel to the optical axis after passing through the sample, while in presence of scattering substances the collimated light rays will diverge from the optical axis with an angle proportional to the concentration of the scattering substance.

Sensitivity of an assay is the change in transmission as a function of the concentration of a substance in the sample causing the change, compared to a reference, e.g., a blank solution. More sensitive to scattering means larger change in transmission at parity of concentration. Particularly, a scattering assay is said to be sensitive if small changes in transmission can be detected, i.e., if light diverging from the optical axis with an angle less than about 5 degrees, typically less than about 3 degrees, can be detected, wherein the smaller the angle the more sensitive to scattering the assay will be. Thus, the light angle selector is being adjusted to prevent only light diverging from the optical axis with an angle less than about 5 degrees to reach the detector, or in other words, to block light with an angle larger than 5 degrees, when a scattering assay is being performed. In order to perform very sensitive scattering assays the angle should be reduced as much as possible, e.g., blocking light transmitted through the sample and diverging from the optical axis with an angle greater than 1 degree.

An assay is said to be insensitive to scattering if light diverging from the optical axis with an angle greater than about 5 degrees can be detected, wherein the greater the angle the more insensitive to scattering the assay will be. In particular, if an absorbance assay, which is insensitive to scattering interferences, has to be performed, it is important that as much light as possible, preferably all the light being emanated from the sample is detected, thus regardless of the angle. In practice, it is technically difficult or expensive to detect angle divergences greater than about 60 degrees. Thus, the light angle selector is being adjusted to allow light transmitted through the sample and diverging from the optical axis with an angle less than about 60 degrees to reach the detector when an absorbance assay is being performed.

A light angle selector according to an embodiment of the invention is therefore a device which enables selecting which light rays transmitted through the sample are being detected depending on the assay type, i.e., scattering or absorbance assay, and desired sensitivity to scattering.

According to one embodiment, the light angle selector comprises a diaphragm with variable aperture, the diaphragm being configured to vary the aperture according to the assay type and the desired sensitivity to scattering, the smaller the aperture the higher the sensitivity to scattering. In this embodiment the optical path typically comprises a focusing lens located between the sample holding position and the diaphragm, wherein the distance between the focusing lens and the diaphragm corresponds to the focal length (f). The distance between the sample holding position and the focusing lens is of minor importance as far as it is sufficiently large to receive all the light emanated from the sample. Practically, in order to avoid the use of large lenses and therefore incur larger costs, the distance is typically limited to a few millimeters.

A lens with a focal length (f), combined with a diaphragm at a distance (f) from the lens, and having an aperture with radius (r), achieves a cut-off angle ($\alpha$) that is equal to the arcsine of r/f ($\alpha$=arcsin r/f). In other words, light rays having an angle greater than $\alpha$ with respect to the optical axis will be blocked, i.e., prevented to reach the detector, while light rays having an angle smaller than $\alpha$ will pass through the aperture and thus reach the detector. Adjusting the light angle selector means in this case varying the aperture of the diaphragm. Since the focal length is typically a property of the lens used and f is thus fixed, varying the aperture radius (r) will provide a different angle selection, the smaller the radius the smaller the angle of the light allowed to pass through the aperture, thus the higher the sensitivity to scattering.

According to a variant of this embodiment, the light angle selector comprises an LCD (Liquid Crystal Display) with switchable pixels, each pixel being configured to be switched off such as to block light or to be switched on such as to form a transparent aperture in a central section of LCD allowing light to pass through according to the assay type and the desired sensitivity to scattering, the smaller the aperture formed, i.e., the smaller the number of pixels in the central section allowing light to reach the detector the higher the sensitivity to scattering. The principle on which LCDs work, making use of, e.g., polarizing layers, is well known and not further elucidated here. Of course, it is also possible to divide the LCD in different sections, e.g., at least two sections, for providing two apertures: one small section switched on in the center for providing a small aperture to allow only light diverging from the optical axis with an angle less than about 5 degrees to reach the detector, and one section surrounding the central section, providing a larger aperture when switched on to allow light of larger angle to reach the detector. Thus, a pixel is defined in general as a switchable section of the LCD, which may assume different shape and size.

A similar effect may be achieved, e.g., if using a detector of the CCD or CMOS type wherein only a small section in the center is used to detect light with small cut-off angles, and a larger or full area is used for detecting as much light as possible regardless of the angle.

According to certain embodiments, the light angle selector comprises a group of lenses and a driver for varying the relative distance between lenses as a zoom objective with variable focal length, the objective being configured to vary the focal length according to the assay type and the desired sensitivity to scattering, the longer the focal length the higher the sensitivity to scattering. Particularly, one or more lenses may be coupled to a driver for moving any of these components relative to the others with the effect of varying the focal length. A longer focal length corresponds to light of smaller angle being allowed to reach the detector. The effect is thus the same of that achieved by reducing the aperture radius of a diaphragm with variable aperture. This means that by increasing the focal length, the sensitivity to scattering will also increase.

A diaphragm with fixed or variable aperture may be combined with the group of lenses of the objective, the position of which may vary according to the particular objective design, e.g., according to the focal length range.

According to one embodiment, the light angle selector comprises a driver for varying the relative distance between the sample holding position and the detector, the driver being configured to vary the distance according to the assay type and the desired sensitivity to scattering, the larger the distance the higher the sensitivity to scattering.

According to another embodiment, the driver is coupled to the detector to vary the distance of the detector with respect to the sample holding unit.

Moving the detector has an effect comparable to that of varying the aperture of a diaphragm. The sensitive part of the detector receiving the light, i.e., the sensor's surface, is analogous to an aperture, which allows light of increasing angle to be detected as it gets closer to the sample holding position. This is analogous to a large aperture when compared to the embodiment comprising a diaphragm with variable aperture or to a short focal length when compared to the embodiment comprising an objective with variable focal length. Analogously, if the distance between the detector and the sample holding position is increased, only light with small angles of divergence will reach the detector. This can be compared to a small aperture in the embodiment comprising a diaphragm with variable aperture or to a long focal length in the embodiment comprising an objective with variable focal length. Thus, when a scattering assay is being performed the distance between the detector and the sample holding position will be adapted such as to allow only light transmitted through the sample and diverging from the optical axis with an angle less than about 5 degrees to reach the detector. The exact distance and thus the angle will depend on the area of the surface detector as well as on the desired sensitivity of the scattering assay, the further the distance the more sensitive being the assay. On the other hand, when an absorbance assay is being performed the distance between the detector and the sample holding position will be adapted such as to allow light transmitted through the sample and diverging from the optical axis with an angle less than about 60 degrees to reach the detector.

Although the above embodiment has been described with reference to the detector moving relative the sample holding position, the sample holding position may move relative to the detector or both may move relative to each other.

Drivers may be arranged as a linear stage or arm driven by a motor along a line parallel to the optical axis, to which one or more moving components are attached. Adaptations are of course possible depending on the elements to be moved and the direction of movement.

It is also possible to combine different embodiments, wherein, for example, the light angle selector comprises a combination of at least two elements chosen from a group comprising a diaphragm with variable aperture, at least one lens, one or more drivers for varying the focal length and/or the relative distance between the sample holding position and the detector. Alternatively, the light angle selector may comprise a combination of at least two elements chosen from a group comprising an LCD with switchable pixels, at least one lens, one or more drivers for varying the focal length and/or the relative distance between the sample holding position and the detector along the optical axis.

According to one typical embodiment, the optical system comprises a control unit for automatically adjusting the light angle selector according to the assay type and/or particular assay parameters to be determined. The control unit may be embodied as a programmable logic controller running a computer-readable program provided with instructions to perform operations in accordance with the process operation plan.

The control unit may be set up to automatically determine an assay sequence, i.e., the order in which a number of assays are carried out, based on the assay type and/or particular assay parameters to be determined. In this way the overall workflow may be optimized by avoiding, e.g., time gaps due to the readjustment of the optical system when different assay types have to be performed for a given sample or set of samples.

The present invention in accordance with yet another embodiment also refers to an instrument for performing scattering and absorbance assays in clinical diagnostics, the instrument comprising the optical system defined herein.

An instrument according to an embodiment of the present invention is an apparatus assisting users with the detection, e.g., qualitative and/or quantitative optical evaluation of samples for diagnostic purposes. Examples of such an instrument are: a clinical chemistry analyzer, a coagulation chemistry analyzer, an immunochemistry analyzer, a urine analyzer, either as self-standing instrument or module within a system comprising a plurality of said modules, used to detect the result of chemical or biological reactions or to monitor the progress of chemical or biological reactions.

In particular, the instrument may comprise units assisting with the pipetting, dosing, mixing of samples and/or reagents, units for loading and/or unloading and/or transporting and/or storing sample tubes or racks comprising sample tubes, units for loading and/or unloading and/or transporting and/or storing reagent containers or cassettes. The analyzer may also comprise identification units comprising sensors, e.g., barcode readers. Alternative technologies such as RFID may also be used for identification.

According to one typical embodiment, the instrument further comprises a sample receiving unit for receiving samples to be assayed. Samples may be received for example in the form of tubes, e.g., blood collection tubes, or smaller tubes or vessels comprising sample aliquots. Samples may be arranged in single carriers or holders or racks for multiple samples.

According to another typical embodiment, the instrument further comprises a reagent holding unit for holding reagents to perform the assays. Reagents may be arranged for example in the form of containers or cassettes containing individual reagents or group of reagents, placed in appropriate receptacles or positions within a storage compartment or conveyor.

According to yet another typical embodiment, the instrument further comprises a cuvette feeding unit for feeding optical cuvettes to the sample holding unit.

According to still yet another typical embodiment, the instrument further comprises a liquid processing unit, e.g., a pipetting unit, to deliver samples and/or reagents to optical cuvettes. The pipetting unit may comprise a reusable washable needle, e.g., a steel needle, or disposable pipette tips. Typically, the pipetting unit is operatively coupled to an automated positioning device for moving the pipette tip or needle with respect to the instrument and, e.g., may be mounted to a transfer head that can be moved in two directions of travel in a plane, e.g., by means of guiding rails and a third direction of travel orthogonal to the plane, e.g., by means of a spindle drive.

The instrument may further comprise incubation units for maintaining sample/reagent mixtures at a certain temperature during reaction, wash stations for washing pipette tips or needles, mixing paddles, etc.

According to a typical embodiment, the instrument comprises a control unit for automatically determining an assay sequence, i.e., the order in which a number of assays are carried out, based on the assay type and/or particular assay parameters to be determined. The control unit may be embodied as a programmable logic controller running a computer-readable program provided with instructions to perform operations in accordance with the process operation plan. The same control unit may also control the light angle selector of the optical system or cooperate with a second control unit of the optical system.

According to one embodiment the instrument comprises a plurality of optical systems.

The present invention also relates to a method for performing scattering and absorbance assays in clinical diagnostics, the method comprising the steps of:

emitting from a light source collimated light parallel to an optical axis in an optical path, measuring light with a detector transmitted through a sample being located in the optical path in a sample holding unit, adjusting a light angle selector such as to prevent light transmitted through the sample and diverging from the optical axis with an angle greater than a value comprised between 0.1 and about 5 degrees from reaching the detector when a scattering assay is being performed, adjusting said light angle selector such as to allow light transmitted through the sample and diverging from the optical axis with an angle smaller than about 60 degrees to reach the detector when an absorbance assay is being performed.

According to a typical embodiment, the method comprises the step of automatically adjusting the light angle selector according to the assay type and/or particular assay parameters to be determined.

According to another typical embodiment, adjusting the light angle selector comprises the step of varying the aperture of a diaphragm according to the assay type and the desired sensitivity to scattering, the smaller the aperture the higher the sensitivity to scattering.

According to yet another typical embodiment, the method comprises the step of varying the relative distance between lenses such as to vary focal length according to the assay type and the desired sensitivity to scattering, the longer the focal length the higher the sensitivity to scattering.

According to still yet another typical embodiment, the method comprises the step of varying the relative distance between the sample holding position and the detector along the optical axis according to the assay type and the desired sensitivity to scattering, the larger the distance the higher the sensitivity to scattering.

According to still yet another typical embodiment, the method further comprises the step of automatically determining an assay sequence, i.e., the order in which a number of assays are carried out, based on the assay type and/or particular assay parameters to be determined. For example, if through-put is an issue, in order to avoid the continuous readjustment of the optical system, with possible consequent waiting times, a certain number of assays of the same type may be performed before changing to the second type of assay. Priorities may be also automatically set according to the type of sample and parameters to be determined, e.g., according to the stability of the sample.

In order that the invention may be more readily understood, reference is made to the following examples, which are intended to illustrate the invention, but not limit the scope thereof.

FIG. 1 depicts schematically an optical system 100 for performing scattering and absorbance assays in clinical diagnostics. The optical system 100 comprises a light source 60. The light source 60 comprises a light emitting element 61 such as, e.g., a halogen lamp and a collimator 63, such as a collimating lens, for collimating the light emitted by the light emitting element 61. The collimated light 50 is parallel to an optical axis 51 of an optical path 51'. The direction of the light is indicated by arrows along the optical path 51'. The optical system 100 further comprises a sample holding unit 21 comprising a sample holding position 22 for holding an optical cuvette 20 comprising a sample 10 in the optical path 51'. The optical system 100 further comprises an optical detector 70, comprising an array optical sensor 71 such as a CCD sensor, which converts electro-magnetic energy into an electrical signal. The optical system 100 further comprises an adjustable light angle selector 55, wherein said light angle selector 55 is being adjusted to prevent light 50' transmitted through the sample 10 and diverging from the optical axis 51 with an angle greater than a value comprised in a predefined range from reaching the detector 70 when a scattering assay is being performed and wherein said light angle selector 55 is being adjusted to allow light 50' transmitted through the sample 10 and diverging from the optical axis 51 with an angle smaller than a predefined value to reach the detector 70 when an absorbance assay is being performed. The optical system 100 further comprises optical path components such as lenses 52, apertures 53, mirrors 54 and a diffraction grating 56, which is configured to receive light 67 selected by the light angle selector 55 and disperse it into multiple spectral components 68. The sensor 71 is divided in sectors, each of which dedicated to a wavelength range.

Figure 2:
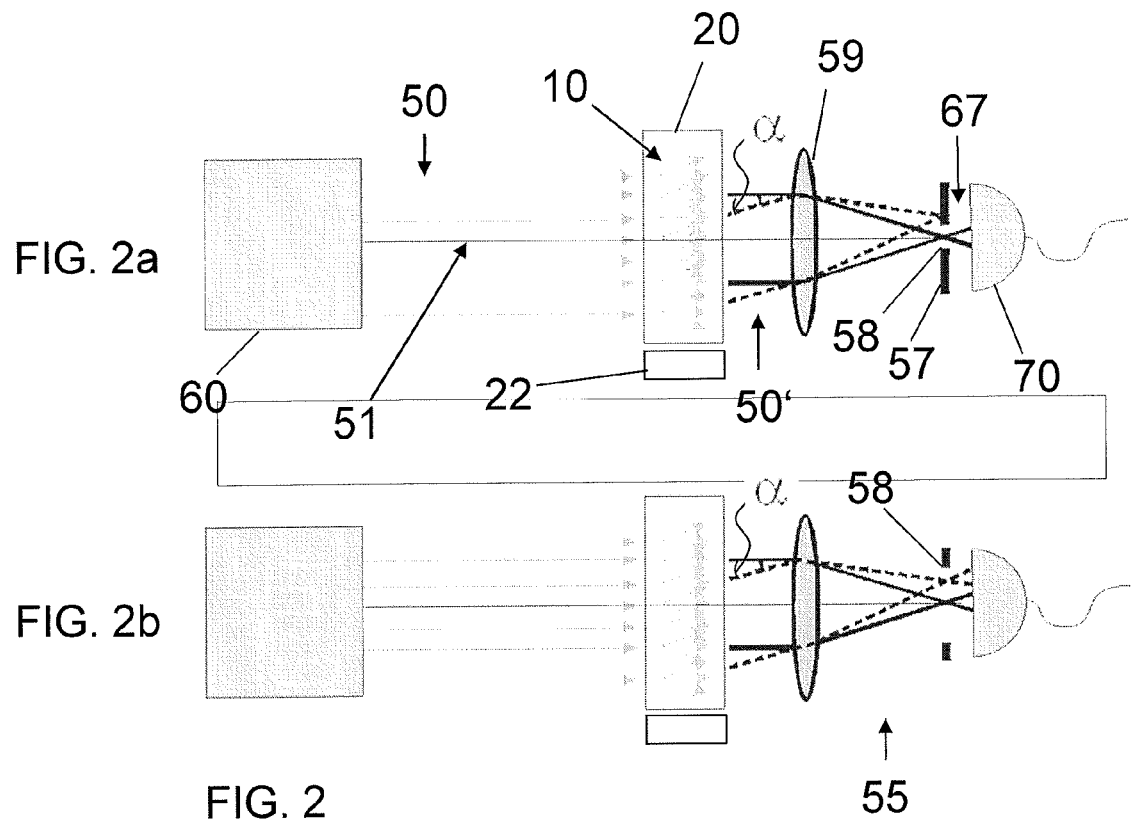
FIGS. 2a and 2b depict schematically an optical system according to an embodiment of the present invention with a first type of adjustable light angle selector.

FIGS. 2a and 2b depict schematically an optical system with a first type of adjustable light angle selector 55. A light source 60 provides collimated light 50 parallel to the optical axis 51. Collimated light 50 is transmitted through a sample 10 contained in an optical cuvette 20 in a sample holding position 22. Due to the presence of scattering substance in the sample 10 the light 50 is scattered, i.e., diverged from the optical axis 51. This is represented by small arrows pointing is different directions in the sample 10. According to this embodiment, the light angle selector 55 comprises a diaphragm 57 with variable aperture 58.

FIG. 2a represents an embodiment when a scattering assay is being performed. Here the aperture 58 is being adjusted, e.g., reduced, to allow light 50' transmitted through the sample 10 and only light 50' diverging from the optical axis 51 with an angle ($\alpha$) smaller than 5 degrees to reach the detector 70.

FIG. 2b represents an embodiment when an absorbance assay is being performed, the aperture 58 being adjusted, e.g., enlarged, to allow light 50' transmitted through the sample 10 and diverging from the optical axis 51 with an angle ($\alpha$) smaller than a predefined value, i.e., smaller than 60 degrees to reach the detector 70. Thus, even if scattering particles are present, virtually all light 50' transmitted through the sample 10 will reach the detector 70 and the extinction measured can be related to absorbance.

Thus, the diaphragm 57 is being configured to vary the aperture 58 according to the assay type, i.e., scattering or absorbance, and the desired sensitivity to scattering, the smaller the aperture the higher the sensitivity to scattering.

Figure 3:
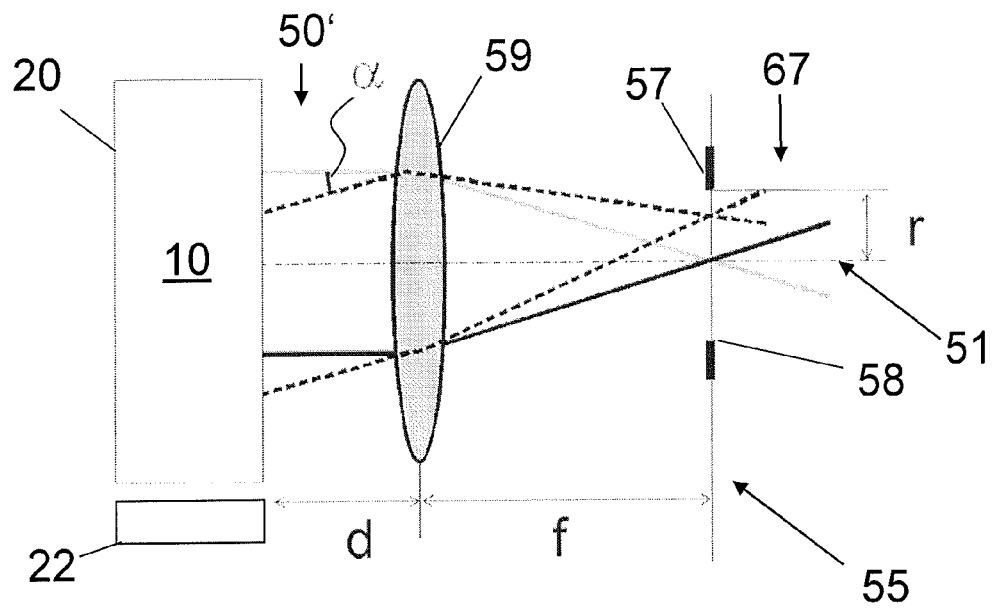
FIG. 3 depicts schematically the relationship between optical parameters in determining light angle selection according to one embodiment of the present invention.

In FIGS. 2a and 3, a focusing lens 59 is shown, located between the sample holding position 22 and the diaphragm 57. FIG. 3 is a magnification of the light angle selector 55 of the type shown in FIGS. 2a and 2b. The diaphragm 57 is located at a distance from the focusing lens 59 that corresponds to the focal length (f) of the lens 59. With a focusing lens 59 having a focal length (f) and a diaphragm 57 at a distance (f) from the lens 59 and having an aperture 58 with radius (r), it is possible to obtain an angle cut-off ($\alpha$) that is equal to the arcsine of r/f ($\alpha$=arcsin r/f). In other words, light rays having an angle greater than $\alpha$ will be blocked, i.e., prevented to reach the detector 70, while light rays having an angle smaller than $\alpha$ will pass through the aperture 58 and thus reach the detector 70. The distance (d) between the sample holding position 22 and the focusing lens 59 is of minor importance as far as it is sufficiently large to receive all the light emanated from the sample 10. Practically, in order to avoid the use of large lenses and therefore incur larger costs, the distance (d) is limited to a few millimeters. Adjusting the light angle selector 55 means, in this case, varying the aperture 58 of the diaphragm 57. Since the focal length (f) is a property of the lens 59 used and (f) is thus fixed, varying the aperture radius (r) will provide a different angle selection, the smaller the radius (r) the smaller is the angle ($\alpha$) of the light allowed to pass through the aperture 58, thus the higher is the sensitivity to scattering. In particular, for a scattering assay an angle ($\alpha$) smaller than 5 degrees will be selected. By using for example a lens with focal length (f) of 7 mm, an aperture 58 with a radius (r) of about 0.6 mm would be required in order to obtain a cut-off angle ($\alpha$) of 5 degrees. In order to carry out a very sensitive scattering assay an angle ($\alpha$) smaller than 1 degree, e.g., closer to 0.1 degrees, will be selected. In order to obtain an angle cut-off ($\alpha$) of, e.g., 0.1 degrees, an aperture 58 with a radius (r) of about 0.01 mm would be required. In order to carry out a less sensitive scattering assay an angle ($\alpha$) closer to 5 degrees will be selected. Typically an angle ($\alpha$) between, e.g., 1 and 3 degrees, will be selected. In order to carry out an absorbance assay an angle ($\alpha$) typically less than 60 degrees, will be selected. This corresponds to an aperture 58 with a radius (r) of about 6 mm or less. This means that light with an angle ($\alpha$) smaller than 60 degrees will be allowed to pass through the aperture 58 and thus reach the detector 70. Although, in principle angles ($\alpha$) below 5 degrees could be selected when performing an absorbance assay, angles ($\alpha$) larger than 5 degrees are typical in order to avoid possible interferences due to undesired scattering substances.

Figure 4:
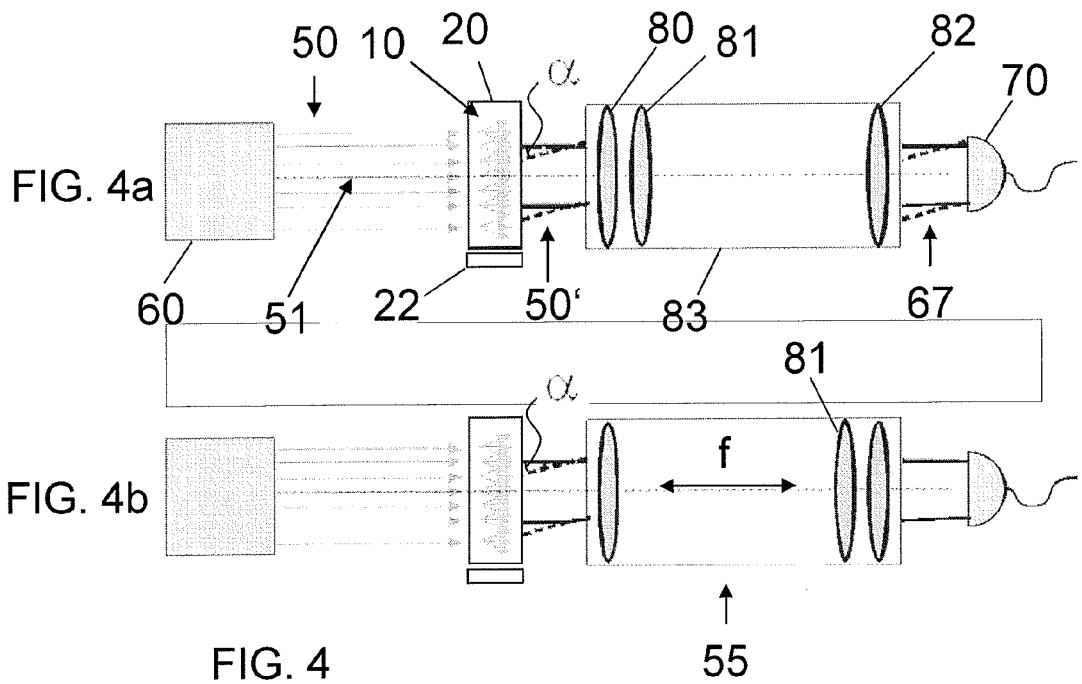
FIGS. 4a and 4b depict schematically an optical system according to an embodiment of the present invention with a second type of adjustable light angle selector.

FIGS. 4a and 4b depict schematically an optical system with a second type of adjustable light angle selector 55. Only differences with respect to the previous embodiment of FIGS. 2a, 2b and 3 will be explained. According to this embodiment, the light angle selector 55 comprises a group of lenses 80, 81, 82 and a driver (not shown) for varying the relative distance between lenses 80, 81, 82 as a zoom objective 83 with variable focal length f. The objective 83 is configured to vary the focal length (f) according to the assay type and the desired sensitivity to scattering, the longer the focal length (f) the higher the sensitivity to scattering. In this particular example three lenses 80, 81, 82 are represented wherein moving the central lens 81 with respect to the other two 80, 82, has the effect of varying the focal length f. A different number of lenses and/or moving parts may however be used. Typically, the objective 83 comprises also an aperture or diaphragm with variable aperture (not shown), the actual position varying depending on the particular optical construction and number of lenses.

FIG. 4a represents an embodiment when a scattering assay is being performed, wherein the objective 83 is being adjusted, i.e., the focal length (f) increased, to allow only light 50' transmitted through the sample 10 and diverging from the optical axis 51 with an angle ($\alpha$) smaller than 5 degrees to reach the detector 70.

FIG. 4b represents an embodiment when an absorbance assay is being performed, the focal length (f) being adjusted, i.e., reduced, to allow light 50' transmitted through the sample 10 and diverging from the optical axis 51 with an angle (α) smaller than a predefined value, i.e., at least 60 degrees to reach the detector 70.

A longer focal length (f) corresponds to light of smaller angle (α) being allowed to reach the detector 70. This means that when increasing the focal length (f) also the sensitivity to scattering will increase, which is analogous to the effect achieved by reducing the aperture radius (r) of the diaphragm 57 with variable aperture 58, shown in FIGS. 2a, 2b and 3.

Figure 5:
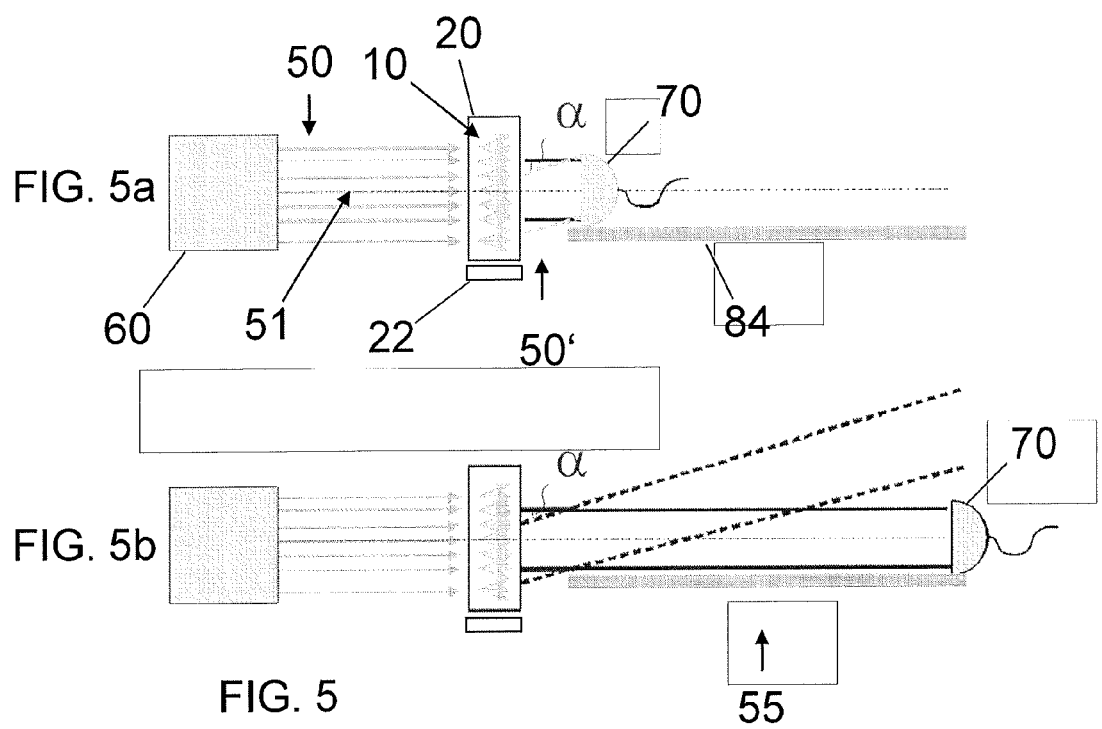
FIGS. 5a and 5b depict schematically an optical system according to an embodiment of the present invention with a third type of adjustable light angle selector.

FIGS. 5a and 5b depict schematically an optical system with a third type of adjustable light angle selector 55. Only differences with respect to the previous embodiments of FIGS. 2a to 4b will be explained. Particularly the light angle selector comprises a driver 84 coupled to the detector 70 to vary the distance (d) of the detector 70 with respect to the sample holding position 22 along the optical axis 51, the distance (d) being varied according to the assay type and the desired sensitivity to scattering, the larger the distance (d) the higher the sensitivity to scattering.

FIG. 5a illustrates the situation when a scattering assay is being performed. The distance (d) between the detector 70 and the sample holding position 22 may be adapted such as to allow only light 50' transmitted through the sample 10 and diverging from the optical axis 51 with an angle (α) smaller than 5 degrees to reach the detector 70. The exact distance (d) and thus the angle (α) will depend on the area of the sensor surface of the detector 70 as well as on the desired sensitivity of the scattering assay; the further the distance (d) the more sensitive the assay.

FIG. 5b illustrates the situation when an absorbance assay is being performed. The distance (d) between the detector 70 and the sample holding position 22 may be adapted such as to allow light 50' transmitted through the sample and diverging from the optical axis 51 with an angle (α) smaller than 60 degrees to reach the detector 70.

Moving the detector 70 has an effect comparable to that of varying the aperture 58 of a diaphragm 57 or the focal length (f) in a zoom objective 83.

FIGS. 6a and 6b refer to a forth type of adjustable light angle selector, replacing the diaphragm 57 shown in FIGS. 2a and 2b. In particular, FIGS. 6a and 6b depict schematically an LCD 57' with switchable pixels represented by black and white squares to indicate a closed (switched off) and an open (switched on) status, respectively. When pixels are open they allow light 50' to pass through and reach the detector 70. When pixels are closed they block light 50', i.e., they prevent light 50' to reach the detector 70. According to this embodiment, the method comprises the step of varying the number of open pixels 58' in the center of the LCD, which allow light to reach the detector 70, according to the assay type and the desired sensitivity to scattering, the smaller the number of open pixels 58' in the center or the larger the open section in the center, the higher the sensitivity to scattering.

FIG. 6a illustrates the situation when a scattering assay is being performed. With a small number of open pixels 58' in the center of the LCD 57' an effect is obtained, which is comparable to that of reducing the aperture 58 of the diaphragm 57 shown in FIG. 2a. The smaller the number of open pixels 58', the higher the sensitivity to scattering.

FIG. 6b illustrates the situation when an absorbance assay is being performed. With a large number of open pixels 58' in the center of the LCD 57', typically with all pixels 58' open (not shown) an effect is obtained, which is comparable to that of increasing the aperture 58 of the diaphragm 57 shown in FIG. 2b, virtually allowing all or most of the light 50' to reach the detector 70.

Figure 7:
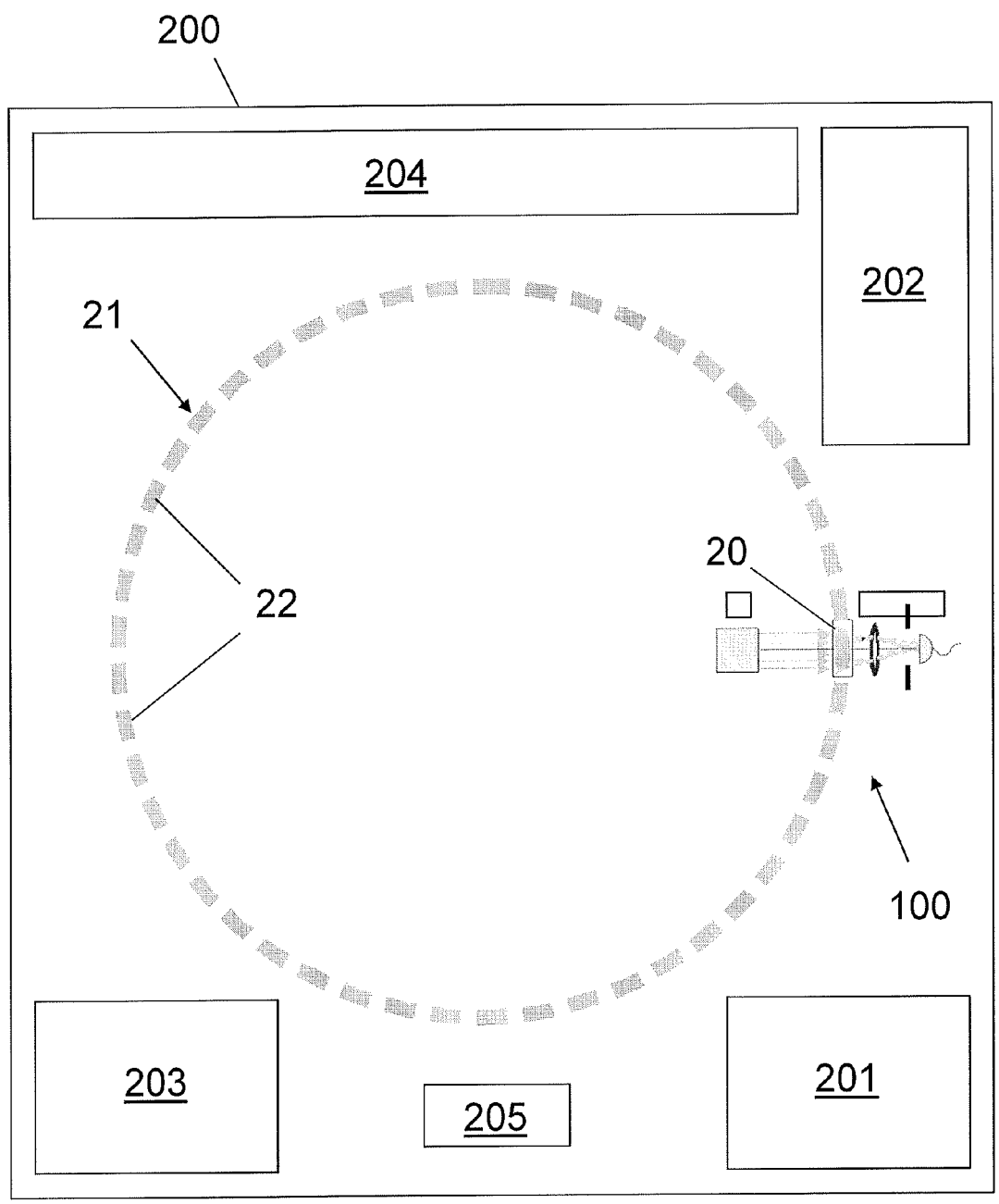
FIG. 7 depicts schematically an instrument according to an embodiment of the present invention for performing scattering and absorbance assays in clinical diagnostics, comprising an optical system with an array of sample holding positions.

FIG. 7 depicts schematically an example of instrument 200 for performing scattering and absorbance assays in clinical diagnostics, comprising an optical system 100 of the type shown in FIGS. 2a and 2b. The optical system 100 comprises a sample holding unit 21 arranged as a rotor comprising an array of sample holding positions 22. The instrument 200 further comprises a sample receiving unit 201 for receiving sample tubes (not shown) comprising samples to be assayed. The instrument 200 further comprises a reagent holding unit 202 for holding reagent containers comprising reagents to perform the assays. The instrument 200 further comprises a cuvette feeding unit 203 for feeding optical cuvettes to the sample holding unit 21. The instrument 200 further comprises a liquid processing unit 204, such as at least one pipetting unit, to deliver samples and/or reagents to optical cuvettes 20. Cuvettes 20 may be temporarily removed from the rotor 21 for addition of samples and/or reagents or for mixing operations by robotic work stations (not shown) located around the rotor 21. The instrument 200 further comprises a control unit 205 for automatically determining an assay sequence based on the assay type and/or particular assay parameters to be determined. The rotor 21 may thus be instructed to locate sample holding positions in the optical path of the optical system 100 one at a time according to an established assay sequence.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An optical system for performing scattering and absorbance assays in clinical diagnostics, the optical system comprising:
    a light source for emitting collimated light parallel to an optical axis in an optical path,
    a sample holding unit comprising at least one sample holding position,
    an optical detector for measuring light transmitted through a sample being located in the optical path in the sample holding position, and
    an adjustable light angle selector comprising at least one of the following:

at least one lens with a focal length (f) and a diaphragm with variable aperture located at the focal length (f) or an LCD with switchable pixels located at the focal length (f), a group of lenses and a driver for varying the relative distance between lenses as a zoom objective with variable focal length (f), and a driver for varying the relative distance between the sample holding position and the detector along the optical axis, wherein for a scattering assay, said adjustable light angle selector through aperture radius, focal length, distance of the detector with respect to the sample holding position or number of open pixels allows only light transmitted through the sample and diverging from the optical axis with an angle ($\alpha$) less than about 5 degrees to reach the optical detector, and for an absorbance assay, said adjustable light angle selector through aperture radius, focal length, distance of the detector with respect to the sample holding position or number of open pixels allows light transmitted through the sample and diverging from the optical axis with an angle ($\alpha$) less than about 60 degrees to reach the same optical detector as for the scattering assay.

2. The optical system according to claim 1, wherein for a scattering assay the light angle selector is adapted to be adjusted such as to allow only light transmitted through the sample and diverging from the optical axis with an angle ($\alpha$) of about 3 degrees or less to reach the detector.

3. The optical system according to claim 1, wherein the diaphragm is configured to vary the aperture according to the assay type and the desired sensitivity to scattering, the smaller the aperture the higher the sensitivity to scattering.

4. The optical system according to claim 1 further comprising a control unit for automatically adjusting the light angle selector according to the assay type and/or particular assay parameters to be determined.

5. A method for performing scattering and absorbance assays in clinical diagnostics, the method comprising the steps of:

emitting collimated light from a light source parallel to an optical axis in an optical path, measuring light with a detector transmitted through a sample being located in the optical path in a sample holding unit, adjusting an aperture of a diaphragm of a light angle selector based on assay type and desired sensitivity to scattering such as to allow only light transmitted through the sample and diverging from the optical axis with an angle ($\alpha$) less than about 5 degrees to reach the detector when a scattering assay is being performed, or adjusting an aperture of a diaphragm of said light angle selector based on assay type and desired sensitivity to scattering such as to allow light transmitted through the sample and diverging from the optical axis with an angle ($\alpha$) less than about 60 degrees to reach the same detector when an absorbance assay is being performed, wherein the smaller the aperture, the higher the sensitivity to scattering.

6. The method according to claim 5 further comprising the step of automatically adjusting the light angle selector according to the assay type and/or particular assay parameters to be determined.

7. The method according to claim 5 further comprising the step of automatically determining an assay sequence based on the assay type and/or particular assay parameters to be determined.

8. An instrument for performing scattering and absorbance assays in clinical diagnostics, the instrument comprising:
the optical system according to claim 1,
a sample holding unit for receiving samples to be assayed,
a reagent holding unit for holding reagents to perform the assays,
a cuvette feeding unit for feeding optical cuvettes to the sample holding unit, and
a liquid processing unit to deliver samples and/or reagents to optical cuvettes.

* * * * *